(12) United States Patent
Friedmann et al.

(10) Patent No.: US 8,426,162 B2
(45) Date of Patent: Apr. 23, 2013

(54) PROCESS AND APPARATUS FOR THE MICROBIAL PRODUCTION OF A SPECIFIC PRODUCT AND METHANE

(75) Inventors: Hans Friedmann, Scheyern-Fernhag (DE); An-Ping Zeng, Braunschweig (DE)

(73) Assignees: Agraferm Technologies AG, Pfaffenhofen/Ilm (DE); Technische Universitat Hamburg-Harburg, Hamburg (DE); TuTech Innovation GmbH, Hamburg (DE)

( * ) Notice: Subject to any disclaimer, the term of this patent is extended or adjusted under 35 U.S.C. 154(b) by 190 days.

(21) Appl. No.: 12/681,899

(22) PCT Filed: Oct. 8, 2008

(86) PCT No.: PCT/EP2008/063493
§ 371 (c)(1),
(2), (4) Date: Jul. 19, 2010

(87) PCT Pub. No.: WO2009/047275
PCT Pub. Date: Apr. 16, 2009

(65) Prior Publication Data
US 2010/0285548 A1    Nov. 11, 2010

(30) Foreign Application Priority Data
Oct. 8, 2007    (DE) .......................... 10 2007 048 277

(51) Int. Cl.
*C12P 39/00* (2006.01)
*C12P 7/54* (2006.01)
*C12P 5/02* (2006.01)
*C12P 7/18* (2006.01)

(52) U.S. Cl.
USPC .............. 435/42; 435/140; 435/158; 435/167

(58) Field of Classification Search ................... 435/140, 435/158, 167, 303.1, 42
See application file for complete search history.

(56) References Cited

U.S. PATENT DOCUMENTS

| 4,288,550 A | 9/1981 | Ishida et al. |
| 4,359,533 A * | 11/1982 | Wilke et al. .................. 435/161 |

(Continued)

FOREIGN PATENT DOCUMENTS

| DE | 3924423 A1 | 1/1991 |
| DE | 10327954 A1 | 1/2005 |

(Continued)

OTHER PUBLICATIONS

Kusel et al "Clostridium scatologenes strain SL1 isolated as an acetogenic bacterium from acidic sediments" International Journal of Systemactic and Evolutionary Microbiology (2000), 50, 537-546.*

(Continued)

*Primary Examiner* — Jon P Weber
*Assistant Examiner* — Charles Zoltan Constantine
(74) *Attorney, Agent, or Firm* — Rankin, Hill & Clark LLP (57) ABSTRACT

The process according to the invention for the microbial production of a specific product and methane comprises the following steps: a) the production in a bioreactor (2, 10) of a specific product from a specific substrate using a specific organism, the producer, wherein during the production of this product metabolites such as e.g. low-molecular alcohols, aldehydes and acids, hydrogen and $CO_2$, which may inhibit the production of the product, are obtained; and b) the production of methane by means of a methanogen, wherein in the production of the methane at least one metabolite is decomposed and by this means removed from the bioreactor (2, 10) and its energy is made usable.

12 Claims, 5 Drawing Sheets

U.S. PATENT DOCUMENTS

| | | | | | |
|---|---|---|---|---|---|
| 4,460,687 | A | * | 7/1984 | Ehnstrom | 435/161 |
| 4,919,813 | A | * | 4/1990 | Weaver | 210/603 |
| 5,599,689 | A | * | 2/1997 | Haynie et al. | 435/42 |
| 5,670,345 | A | * | 9/1997 | Srivastava et al. | 435/75 |
| 6,328,959 | B1 | | 12/2001 | Kayar et al. | |
| 2005/0069997 | A1 | * | 3/2005 | Adkesson et al. | 435/158 |
| 2006/0177914 | A1 | | 8/2006 | Rollmann et al. | |
| 2007/0161077 | A1 | | 7/2007 | Pfeiffer et al. | |
| 2009/0098598 | A1 | | 4/2009 | Filho et al. | |

FOREIGN PATENT DOCUMENTS

| | | |
|---|---|---|
| DE | 102007001614 A1 | 7/2008 |
| WO | 2006/021087 A1 | 3/2006 |

OTHER PUBLICATIONS

Biebl et al "Glycerol conversion to 1,3-propanediol by newly isolated clostridia" Appl Microbiol Biotechnol (1992) vol. 36 p. 592-597.*

Smiti et al "Thermophilic degradation of cellulose by a triculture of *Clostridium thermocellum, Methanobacterium* sp. and *Methanosarcina* MP", FEMS Microbiology Letters 35 (1986) 93-97.*

Finn et al. "A Membrane Reactor for Simultaneous Production of Anaerobic Single-Cell Protein and Methane" Separation, Recovery, and Purification in Biotechnology, ACS Symposium Series, vol. 314 (1986) Chapter 4, pp. 43-49.*

International Search Report for corresponding PCT/EP2008/063493 mailed Aug. 6, 2009, 8 pages.

Computer Translation for DE 39 24 423 A1, 14 pages.

Computer Translation for DE 10 2007 001614 A1, 13 pages.

Computer Translation for DE 10 327 954 A1, 14 pages.

Jones et al "Acetone-Butanol Fermentation Revisited," Microbiological Reviews, Dec. 1986, vol. 50, No. 4, pp. 484-524.

Menzel et al. "Enzymatic evidence for an involvement of pyruvate dehydrogenase in the anaerobic glycerol metabolism of *Klebsiella pneumoniae*," Journal of Biotechnology, 1997, vol. 56, pp. 135-142.

Diekert et al. "Carbon monoxide fixation into the carboxyl group of acetate during growth of *Acetobacterium woodii* on H2 and CO2," FEMS Microbiology Letters, 1983, vol. 17, pp. 299-302.

* cited by examiner

$$\begin{pmatrix} 1 & -1 & -1 & 1 & 0 & 0 & 0 & 1 \\ 0 & 0 & 1 & -1 & -1 & 0 & 0 & 0 \\ 0 & 0 & 0 & 0 & 1 & -1 & -1 & 0 \\ 1 & 0 & 0 & 0 & 0 & 0 & 0 & 0 \\ 0 & 0 & -K_{1,i} & 1 & 0 & 0 & 0 & 0 \\ 0 & 0 & 0 & 0 & -K_{2,i} & 1 & 0 & 0 \\ 0 & 0 & 0 & 0 & 0 & 0 & 0 & 1 \\ 0 & 1 & -K_{purge} & 0 & 0 & 0 & 0 & 0 \end{pmatrix} \cdot \begin{pmatrix} m_{i,0} \\ m_{i,1} \\ m_{i,2} \\ m_{i,3} \\ m_{i,4} \\ m_{i,5} \\ m_{i,6} \\ m_{i,7} \end{pmatrix} = \begin{pmatrix} 0 \\ 0 \\ 0 \\ m_{i,input} \\ 0 \\ 0 \\ m_{i,reaction} \\ 0 \end{pmatrix} \quad (1)$$

$$\begin{pmatrix} 1 & -1 & -1 & 1 & 0 & 0 & 0 & 1 \\ 0 & 0 & 1 & -1 & -1 & 0 & 0 & 0 \\ 0 & 0 & 0 & 0 & 1 & -1 & -1 & 0 \\ 1 & 0 & 0 & 0 & 0 & 0 & 0 & 0 \\ 0 & 0 & -K_{1,i} & 1 & 0 & 0 & 0 & 0 \\ 0 & 0 & 0 & 0 & -K_{2,i} & 1 & 0 & 0 \\ 0 & 0 & 0 & 0 & 0 & 0 & 0 & 1 \\ 0 & 1 & 0 & 0 & 0 & 0 & 0 & 0 \end{pmatrix} \cdot \begin{pmatrix} m_{i,0} \\ m_{i,1} \\ m_{i,2} \\ m_{i,3} \\ m_{i,4} \\ m_{i,5} \\ m_{i,6} \\ m_{i,7} \end{pmatrix} = \begin{pmatrix} 0 \\ 0 \\ 0 \\ m_{i,input} \\ 0 \\ 0 \\ m_{i,reaction} \\ -m_{i,reaction} \end{pmatrix} \quad (2)$$

PROCESS AND APPARATUS FOR THE MICROBIAL PRODUCTION OF A SPECIFIC PRODUCT AND METHANE

TECHNICAL FIELD

The present invention relates to a process and an apparatus for the microbial production of a specific product and methane. In one embodiment of the invention, the product is 1,3-propanediole.

PRIOR ART 1,3-propanediol (PDO) is a monomer used in the production of polyesters for fibres and films and has a range of further applications in chemistry. It is known for PDO to be produced in a chemical-synthetic two-stage process, which involves a cobalt-catalysed hydroformylation (conversion with synthesis gas $H_2/CO$) of ethylene oxide to the intermediary 3-hydroxypropanal (HPA) and a hydration of HPA to PDO. The initial stage of the hydroformylation is made at temperatures of over 100° C. and high synthesis gas pressures, in order to obtain practicable reaction times. However, the resulting product mixture gives only a low HPA yield.

Known from EP 0 888 266 is a chemical-synthetic process for the production of 1,3-propanediol. The purification is effected by means of a cobalt-catalysed process without using a phosphinate ligand for the cobalt catalyst. It is also claimed that the extent of recovery and recycling of the cobalt catalyst is improved. This process is however very costly in terms of energy, uses toxic chemicals and runs under high pressures of 70 bar to 240 bar.

1,3-propanediol may also be produced using a microbial process.

WO 03/104471 describes a microbial process for the production of 1,3-propanediol. Here it is provided for the 1,3-propanediol to be produced by fermentation from glycerol by means of a medium containing sulphur.

Further microbiological processes for producing 1,3-propanediol from glycerol are disclosed in EP 0 648 273 B1 (DE 693 04 332 Pt 2) and EP 0 373 230 B1 (DE 38 78 564 Pt T2).

The microbial production of 1,3-propanediol is described in the postdoctoral thesis of Zeng (Zeng 2000, Quantitative Zellphysiologie [Quantitative Cell Physiology], Metabolic Engineering and Modelling of Glycerol Fermentation to 1,3-propanediol. Technical University of Braunschweig).

Described in DE 39 24 423 is a microbial process for the conversion of glycerol into 1,3-propanediol by means of microorganisms. This process is said to originate in particular with technically occurring glycerol liquids from the technical processing of triglycerides. In this process, a microorganism strain is selected from the species *Clostridia, Enterobacter, Lactobacilli, Bacilli, Citrobacter, Aerobacter*, and *Klebsiella* and converts glycerol into 1,3-propanediol with a space-time yield of more than $0.5\ g\ h^{-1}\ l^{-1}$, on a glycerol solution of 5% by weight as the sole carbon source under standard fermentation conditions. It then uses this, on glycerol as sole carbon source under anaerobic conditions for the technical conversion of glycerol solutions with a concentration of 5 to 20% glycerol by weight, at a constant pH value and, after further consumption of the glycerol, separates the resultant biomass and processes the product mixture by distillation.

Full reference is made to the aforementioned documents, which describe microbial processes for the production of 1,3-propanediol.

DESCRIPTION OF THE INVENTION

The invention is based on the problem of providing a fermentative process and an apparatus for the microbiological production of a specific product with a very high yield, and with very good energy efficiency at low cost.

The problem is solved by the features of the processes and apparatus defined in the patent claims.

The process according to the invention for the microbial production of a specific product and methane comprises (a) the production in a bioreactor of a specific product from a specific substrate using a specific organism, wherein during the production of this product metabolites arise as by-products, such as e.g. low-molecular alcohols, aldehydes and organic acids, hydrogen and $CO_2$, which may inhibit the production of the product; and (b) the production of methane by means of a methanogen or a mixed culture with a methanogen as a constituent, wherein in the production of the methane at least one metabolite is decomposed and by this means removed from the bioreactor.

In one embodiment of the invention the specific product, i.e. the useful substance, and methane are produced together in the same bioreactor, wherein the product is for example 1,3-propanediol. For this purpose a co-culture or a mixed culture of product-generating, methanogenic and, as applicable, acetogenic microorganisms is established in the bioreactor. The various microorganisms of the co-culture are selected so that they may be cultivated under similar processing conditions, in particular pH value, temperature, etc. The fermentation process involving such a co-culture to convert the specific substrate into the specific product and methane is then structured around the hydraulic retention time, biomass retention time, pH, temperature, redox potential, retention time distribution and/or the addition of chemicals.

In an alternative embodiment the bioreactor may be divided into two reactor chambers, for example by a dialysing membrane, with the specific product being created in one reactor chamber, while the metabolites occurring in the course of product formation are converted into methane in the other reactor chamber. In the case of this variant too, the metabolites are continuously removed from the reactor chamber for product creation, therefore promoting the making of the product, while mixed cultures may also be present in both reactor chambers.

In one embodiment a further bioreactor, in which methane is similarly produced, may be connected downstream of the bioreactor in which the specific product is formed. In this downstream bioreactor, the surplus purging and residual substances from the bioreactor for product creation may be further recycled to give additional methane for energy use. Compared to the bioreactor for product creation, such a downstream bioreactor has a distinctly longer retention time, and possesses a biomass retention system in order to provide biocoenosis with a wide product spectrum for the residual conversion to methane.

The invention provides for the conversion into methane of acid, reaction-inhibiting and preferably liquid metabolites and hydrogen, with the methane used for energy.

The energy potential of the metabolites is transferred into an easily handled and easily separated energy carrier, and in this way is removed from the reactor. This energy carrier is methane which is converted in an energy converter into power and/or heat which may be used in the process. The waste heat left over in the energy converter may be used locally in the process for creating the product. This local use of waste heat, which need only be transferred from the energy converter to a column or an evaporator, leads to a high level of efficiency combined with a low cost of production. The power generated is either used directly and/or fed into the mains.

Preferably a metabolite which inhibits creation of the product is decomposed, leading to an increase in the efficiency of production.

The process runs at low reaction temperatures of 30-55° C. At these reaction temperatures, the reaction-inhibiting metabolites are preferably liquid.

The process is environmentally-friendly, since no toxic and/or chemical additives are used.

The product is preferably one of the following:
1,3-propanediol,
2,3-butanediol,
succinate,
xylitol,
acetone,
butanol
lactate,
1,2-propanediol, and
glycerol.

The invention is explained in detail below with the aid of two embodiments in conjunction with the appended drawings which show schematically in:

FIG. 5: a balance model.

1. APPARATUS OF THE FIRST EMBODIMENT

Figure 1:
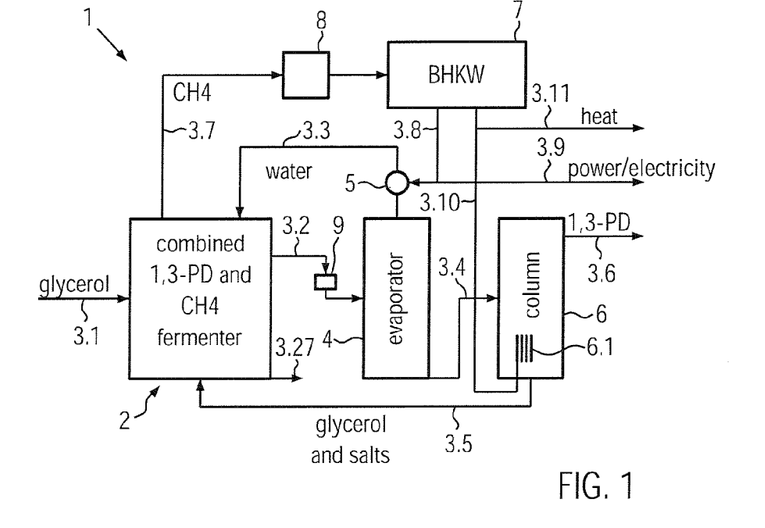
FIG. 1: a circuit diagram of the first embodiment of an apparatus according to the invention for the combined production of 1,3-propanediol and methane.

FIG. 1 shows a preferred embodiment of an apparatus 1 for the combined production of 1,3-propanediol and methane.

Figure 2:
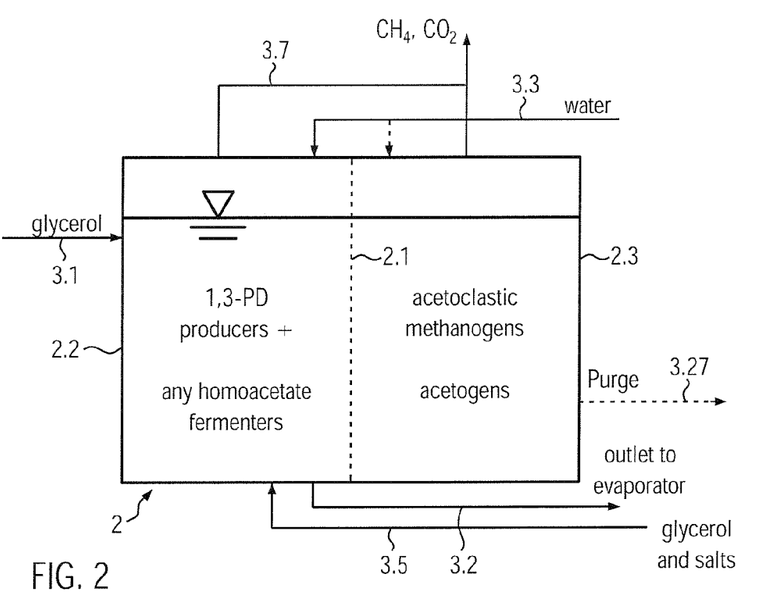
FIG. 2: a sectioned view of a bioreactor of the first embodiment according to the invention, cut away at the side.

The apparatus 1 has a bioreactor 2. The bioreactor 2 may be divided via a vertically arranged dialysing membrane 2.1 into two reactor chambers 2.2, 2.3 (FIG. 2). It is however also possible to use a bioreactor without a membrane, in which a co-culture of product-forming acetogenic and methanogenic microorganisms is established.

The dialysing membrane 2.1 may be either hydraulically permeable (e.g. made of PES) or hydraulically impermeable (e.g. PP). The membrane may be built into the reactor 2 or may be in the form of an external direct or reverse flow dialysing module.

Connected to the one reactor chamber 2.2 for 1,3-propanediol production is a feed line 3.1. In addition, a line section 3.2 leads from the reactor chamber 2.2 to a first separation stage 4. A filter 9 may be integrated in the line section 2.2. The first separation stage 4 is in the form of an evaporator 4.

The evaporator 4 is connected via a line section 3.3 to the reactor chamber 2.2 and the reactor chamber 2.3 for methane production. A compressor 5 is integrated in line section 3.3.

From the evaporator 4, a line section 3.4 leads to a second separation stage 6, which is in the form of a column 6. The column 6 is connected via a line section 3.5 to the reactor chamber 2.2 for 1,3-propanediol production. The column 6 has a discharge line 3.6 and contains a heating device 6.1.

The reactor chamber 2.3 for methane production is connected via a line section 3.7 to an energy converter. Line section 3.7 is located at the top of the container. The energy converter is in the form of a combined heat and power unit.

An outflow 3.27 is also provided on the reactor chamber 2.3.

A line section 3.8 leads from the energy converter 7 to the compressor 5. An outflow line 3.9 branches off from line section 3.8. The energy converter is connected via a line section 3.10 to the heating device 6.1 of the column 6. An outflow line 3.11 branches off from line section 3.10.

Instead of an evaporator 4, the first separation stage 4 may also be in the form of a device for sedimentation, centrifugation, filtration, evaporation, distillation, extraction, absorption, adsorption or membrane separation. A bioreactor downstream of the bioreactor 2 may also be provided, in which the unused purging and residual substances from the bioreactor 2 may be converted to additional methane.

2. APPARATUS OF THE SECOND EMBODIMENT

Figure 3:
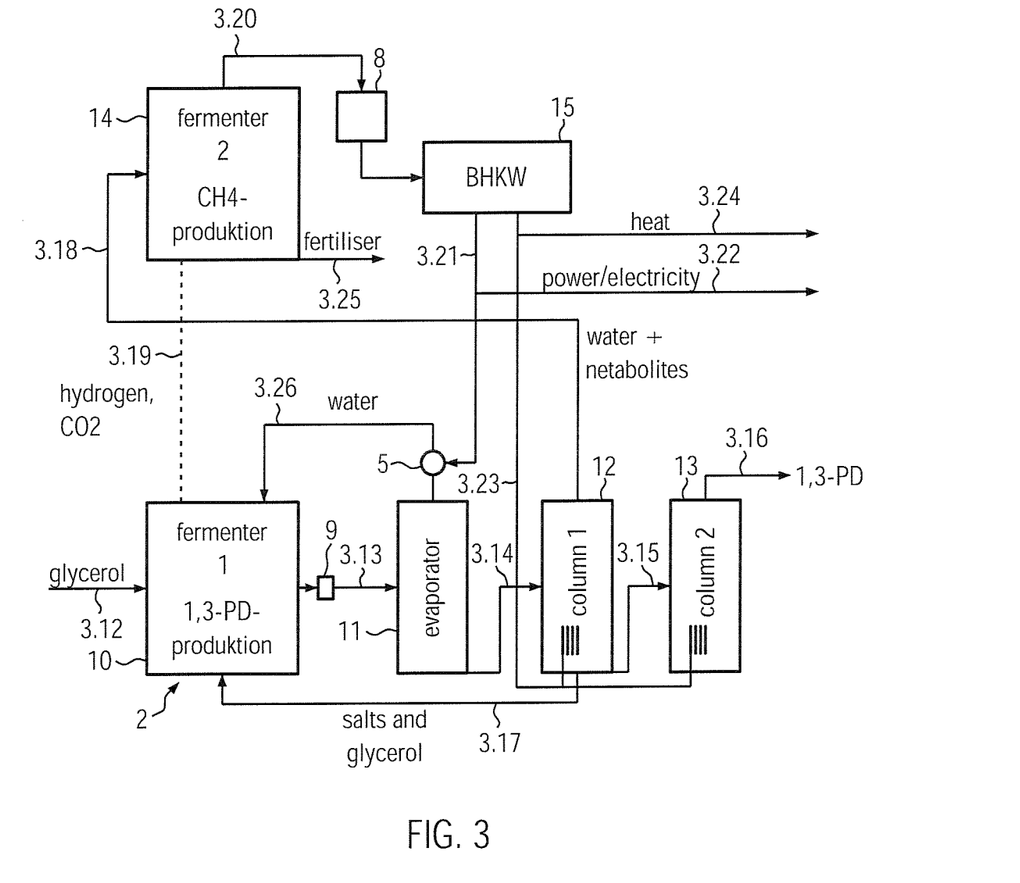
FIG. 3: a circuit diagram of the second embodiment of an apparatus according to the invention for the combined production of 1,3-propanediol and methane.

In contrast to the first embodiment, the second embodiment has two separate bioreactors 10, 14 (FIG. 3). There is no dialysing membrane. Three separation stages are needed for preparation of the fermentation broth.

Connected to the bioreactor 10 for 1,3-propanediol production is a feed line 3.12.

The second bioreactor 14 for methane generation is connected to an energy converter 15 via a line section 3.20. The energy converter 15 is in the form of a combined heat and power unit 15.

The second bioreactor 14 for methane generation has an outflow line 3.25.

Via a second line section 3.13, the bioreactor 10 for 1,3-propanediol production is connected to a first separation stage 11. A filter 9 may be integrated in the line section 3.13. The first separation stage 11 is in the form of an evaporator, which is connected to the bioreactor 10 via a line section 3.26. A compressor 5 is integrated in the line section 3.26.

The first separation stage 11 is connected to a second separation stage 12 by a line section 3.14. The second separation stage 12 is in the form of a column 12.

The second separation stage 12 is connected via a line section 3.15 to a third separation stage 13. A line section 3.16 is connected to the third separation stage 13, which is in the form of a column 13. Via a line section 3.17, the third separation stage is connected to the bioreactor 10 for 1,3-propanediol production.

From the second separation stage 12 a line section 3.18 leads to a second bioreactor 14 for methane production. The first bioreactor 10 for 1,3-propanediol production is connected via a line section 3.19 to the second bioreactor 14 for methane production.

The second bioreactor 14 for methane production has an outflow line 3.25. Via a second line section 3.20, the second bioreactor 14 for methane production is connected to an energy converter 15, which is in the form of a combined heat and power unit 15. A gas storage unit 8 may be integrated in the line section 3.20.

From the combined heat and power unit 15 a line section 3.21 leads to the compressor 5. An outflow line 3.22 is integrated in the line section 3.21. The combined heat and power unit 15 is connected via a line section 3.23 with the second and third separation stages 12, 13. An outflow line 3.24 is integrated in line section 3.23.

3. PROCESS FOR THE PRODUCTION OF 1,3-PROPANEDIOL AND METHANE IN ACCORDANCE WITH THE FIRST EMBODIMENT

The process for the combined production of 1,3-propanediol and methane will be explained below with the aid of the first embodiment.

An aqueous glycerol solution is fed through the feed line 3.1 into the reactor chamber 2.2 for 1,3-propanediol production, in which 1,3-propanediol producers are contained.

The glycerol solution is used as carbon source and energy source and is derived preferably from an effluent or waste flow from fat hydrolysis or transesterification.

Used as 1,3-propanediol producers are for example bacteria of the species *Klebsellia* especially *K. pneumonae* and/or *Enterobacter* especially *E. agglomerans* and/or *Citrobacter*, especially *C. freundii* and/or *Lactobacilli* especially *L. brevis* and/or *L. buchneri* and/or *Clostridia* especially *C. butyricum* and/or *C. pasteurianum* and/or a mixed culture containing these species at least in part.

In addition, an acetogenic bacterium of the species *Acetobacter* and/or *Clostridia*, especially *A. woodi* and/or *C. aceticum* and/or a mixed culture containing the aforementioned bacteria at least in part may be used to convert the metabolites which form. The metabolites are low-molecular alcohols, aldehydes and organic acids which may inhibit either the growth of the 1,3-propanediol producers or the actual 1,3-propanediol production.

Preferably used in reactor chamber 2.3 is an acetogenic bacterium, which converts metabolites of the 1,3-propanediol producers with a molecular weight of <200 g/mol into acetic acid, $H_2$ or $CO_2$.

The following reactions for example take place in reactor chamber 2.2.

Butyric acid+$2H_2O$=>2 acetic acid+$2H_2$(acetogens 2.2)

Propionic acid+$2H_2O$=>acetic acid+$3H_2$+$CO_2$(acetogens 2.2)

Since hydrogen accumulates in the bioreactor in reactor chamber 2.2, a special form of acetogens—so-called homoacetate fermenters—is used as $H_2$ sink. They catalyse the following transformation:

$4H_2$+$2CO_2$=>acetic acid+$2H_2O$

The acetic acid resulting from these transformations diffuses through the membrane 2.1 into the reactor chamber 2.3, where it provides the substrate of the methane bacteria. The following reaction for example may take place:

Acetic acid=>$CO_2$+$CH_4$

In reactor chamber 2.3 slow-growing methanogens are cultivated, for example an archaeon of the species *Methanosaricina* and *Methanothrix*, especially *M. Mazei, M. barkeri* and/or *M. acetivorans* and/or a mixed culture containing these species at least in part.

The inhibition of the 1,3-propanediol producers by metabolites such as acetic acid is abolished, since they are converted by methane bacteria to methane.

The methane passes through line section 3.7 into the combined heat and power unit 7 where it is converted into power and heat.

The purification of the results of fermentation is effected preferably by means of sedimentation, flocculation, centrifugation, filtration, evaporation, distillation, extraction, absorption, adsorption or membrane separation. Moreover, as described in section 6, an additional bioreactor may be connected downstream of bioreactor 2, in which the surplus glycerol is converted into additional 1,3-propanediol, thereby making any separation between glycerol and 1,3-propanediol unnecessary.

The fermentation broth containing 1,3-propanediol passes through line section 3.2, in which a filter 9 may be installed, from reactor chamber 2.2 for concentration in the evaporator 4.

The power generated in the combined heat and power unit 7 supplies the compressor 5 in line section 3.3, via line section 3.8. Through line section 3.3, the compressor 5 creates a vacuum in the evaporator 4. By this means, the fermentation broth in the evaporator 4 is concentrated. The separated vapour condensate passes through line section 3.3 into reactor chamber 2.2 for 1,3-propanediol production. In the reactor chamber 2.2 for 1,3-propanediol production, the vapour condensate dilutes the glycerol, since the 1,3-propanediol producers grow better at a low glycerol concentration.

In cases where a highly nitrogenous glycerol source is used, a nitrogen sink may be provided in the vapour condensate return.

Via line section 3.4, the fermentation broth containing the concentrated 1,3-propanediol reaches the column 6. The heat generated in the energy converter 7 passes through line section 3.10 into the heating element 6.1 of the column 6 and heats up the fermentation broth containing the concentrated 1,3-propanediol. This separates out the more volatile 1,3-propanediol. The column bottom contains the unconverted glycerol and the fermentation salts, some of which may be fed back into reactor chamber 2.2 of bioreactor 2 via line section 3.5. The 1,3-propanediol produced may be taken off via outflow line 3.6 at the head of the column 6.

Via line section 3.9, the power may be withdrawn externally from the combined heat and power unit, while the heat from the combined heat and power unit may be removed externally through line section 3.11.

Methanol which is mostly contained in technical glycerol is broken down by the methane bacteria present in the bioreactor.

4. PROCESS FOR THE PRODUCTION OF 1,3-PROPANEDIOL AND METHANE IN ACCORDANCE WITH THE SECOND EMBODIMENT

The process for the combined production of 1,3-propanediol and methane will be explained below with the aid of the second embodiment.

In the second embodiment, the two anaerobic fermentations take place consecutively. The fermentation of glycerol to produce 1,3-propanediol proceeds in bioreactor 10, and the fermentation of the metabolites to methane takes place in bioreactor 14.

In a reactor without a dialysing membrane according to the second embodiment, the following reactions take place:
Bioreactor 10:

Glycerol=>PDO+acetic acid+butyric acid+$CO_2$+$H_2$

Butyric acid+$2H_2O$=>2 acetic acid+$2H_2$(acetogens)

Propionic acid+$2H_2O$=>acetic acid+$3H_2$+$CO_2$(acetogens)

Purification of the 1,3-propanediol takes place in 3 separation stages 11, 12, 13. Similarly to the process in the first embodiment, the vapour condensate separated out in the first separation stage 11 is transferred via line section 3.26 into bioreactor 10 for dilution of the glycerol.

The 1,3-propanediol production is inhibited mainly by organic acids such as acetic acid and butyric acid. These metabolites are removed in the first column 12 and transferred into bioreactor 14 where they are converted into methane.
Bioreactor 14:

Acetic acid=>$CH_4$+$CO_2$(acetoclastic methanogens)

$4H_2$+$CO_2$=>$CH_4$+$2H_2O$(all methanogens)

Since there is a surplus of $CO_2$, all metabolites can be converted into methane or water.

The difference between the two embodiments is that in the dialysing reactor the hydrogen on the 1,3-propanediol producer side must be consumed by homoacetate fermenters. In a reactor without a dialysis unit, this is done by the methanogens, which represent a more effective hydrogen sink than the homoacetate fermenters.

The waste heat generated in the combined heat and power unit 15 passes via line section 3.23 to the second and third separation stages 12, 13 where it is used to separate off the volatile metabolites (in column 1) and to separate off the product of the 1,3-propanediol (in column 2).

Otherwise the apparatus 2 operates in a similar manner to that described for the first embodiment.

In the apparatus according to the invention, the energy potential of the waste materials is transferred to an easily handled and separated energy carrier. This energy carrier is methane, which is converted in an energy converter into power and heat, which are used in the process. This local use of the waste heat leads to a high level of efficiency and keeps the costs of producing 1,3-propanediol to a minimum.

5. SINGLE-STAGE PROCESS WITH A BIOREACTOR WITH NO MEMBRANE

In the first embodiment referred to above, a bioreactor with a membrane is described. In another embodiment of the invention involving this apparatus, a bioreactor with no membrane is used. This latter embodiment is especially advantageous when the byproducts of the producers of the product concerned can be converted directly into methane by the methanogens. This is particularly advantageous if the by-product which occurs is a fairly large quantity of hydrogen since, owing to the poor solubility of the hydrogen in the fermentation liquid, the hydrogen hardly diffuses at all through the membrane into the chamber 2.3, but instead escapes from the reactor with the waste gas flow. The dissolved hydrogen concentration occurring in chamber 2.2 exceeds 10 Pa, due to the resistance to diffusion through the membrane, and is therefore toxic for some processes (for example propionic acid oxidation).

Moreover it may be expedient to work with just a mixture (co-culture) of producers and methanogens, and without acetogens or without homoacetate fermenters. This is the case when the producer of the useful material has only a narrow metabolite spectrum which is largely metabolised by methanogens, or the useful material may be decomposed by acetogens (for example in ethanol, butanol or lactate production).

So, it is possible in a further third embodiment of the invention to produce 1,3-propanediol and methane in a non-sterile fermentation using a co-culture of 1,3-propanediol producers, acetogenic and methanogenic microorganisms. The 1,3-propanediol producing microorganisms and the acetogenic and methanogenic microorganisms recycling the metabolites may in fact be cultivated at the same pH values and temperatures. The non-sterile conduct of the process makes this co-cultivation fermentation especially advantageous because of its lower cost.

The bioreactor may be run with relatively short biomass retention times, which means that microorganisms harmful to the process, such as for example sulphate-reducing microorganisms, may be washed out of the bioreactor.

The substrate is a glycerol solution, for example technical glycerol. The anaerobic 1,3-propanediol producers which grow in the bioreactor produce from the glycerol as metabolism end-products acetic acid, butyric acid, hydrogen and $CO_2$, ethanol, lactic acid and 1,3-propanediol. In the creation of all these products except for propanediol, energy in the form of ATP is generated, but at the same time NADH is also oxidised to NAD. To maintain the redox balance, propanediol must always be produced in stoichiometrich amounts, since the creation of propanediol is the only reaction in which the NAD can be reduced back to NADH. In order to encourage the 1,3-propanediol production, an excess of glycerol may be supplied.

Through the additional introduction of a methanogenic and acetogenic co-culture into the same reactor as the 1,3-propanediol producers, the metabolites of the 1,3-propanediol production which inhibit the 1,3-propanediol producers, for example acetic acid, butyric acid, ethanol, lactic acid and hydrogen, may be converted into methane and $CO_2$, which are not inhibiting and leave the system in the headspace of the bioreactor, from where they are drawn off. By this means the inhibitors are continually withdrawn from the fermentation and the production of 1,3-propanediol is promoted.

In a particular embodiment of the invention, the co-culture is comprised of *Clostridia*, acetogenic and methanogenic bacteria.

6. PURIFICATION OF 1,3-PROPANEDIOL WITHOUT SEPARATION OF GLYCEROL AND 1,3-PROPANEDIOL

For the purification of 1,3-propanediol, more highly volatile components such as acetic acid, butyric acid, lactic acid and ethanol, together with less volatile components such as glycerol and salts, must be separated out from the aqueous fermentation solution.

In the variants of the first and second embodiments, the highly volatile constituents (water, highly volatile metabolites) are first separated out, followed by separation of the less volatile components (glycerol, salts) in distillation columns. 1,3-propanediol and glycerol are hydrophilic and have very high boiling temperatures, for which reason the separations must run at very high bottom temperatures. Glycerol decomposes to acrolein and water at approx. 180° C. Both decomposition products are highly volatile (boiling point 52° C. and 100° C. respectively). The highly toxic acrolein can also polymerise in the separation column. The 1,3-propanediol-glycerol separation therefore takes place under high vacuum in the first and second embodiments, so that the decomposition reaction can not occur. Moreover, the anions of the metabolites (acetic acid, lactic acid, butyric acid) are able to form insoluble salts with the cations of the salts in the solution, so that the highly volatile metabolites may be carried over into the second column and only drawn off via the head. Apart from this, recirculation of salts and glycerol into the fermenter may lead to a concentration of salts, so that an additional salt sink becomes necessary.

Instead of the high vacuum separation of glycerol and 1,3-propanediol, as described in the first and second embodiments, the purification may also be carried out with particular efficiency without glycerol-propanediol separation and, where applicable, a salt sink.

This is achieved by the downstream connection of another reactor, in which the propanediol-forming biomass recycles the remaining surplus glycerol from the first reactor, and the acetogenic and methanogenic biomass metabolises the remaining metabolites. This downstream reactor may be for example in the form of a stirrer tank cascade or a fed-batch reactor. Preferably this downstream reactor is in the form of a flow pipe. No fresh substrate passes into this downstream reactor; the existing biomass simply decomposes the available substrate and metabolite surplus, and then goes hungry. The typical propanediol producers have a very low Monod constant for glycerol (approx 0.005 g/l), meaning that the microorganism metabolism is not significantly slowed down when the glycerol concentration falls.

The downstream reactor must be so controlled that the biomass does not decompose 1,3-propanediol. For example sulphate-reducing microorganisms could decompose propanediol anaerobically, by oxidising 1,3-propanediol back to 3-hydroxypropanal to 3-hydroxypropionic acid (hydracyl acid). This is then further oxidised via acetaldehyde to acetic acid, with the sulphate-reducing microorganisms obtaining the electrons needed for oxidation from the reduction of the sulphate to $H_2S$. This reaction is stopped when sulphate is no longer available in equimolar amounts. 1,3-propanediol may however also be decomposed anaerobically in the absence of sulphate.

In order to prevent the accumulation of microorganisms which can decompose 1,3-propanediol in the downstream reactor, it is necessary to prevent long retention times or non-selective biomass retention. The downstream reactor is therefore so designed that the 1,3-propanediol decomposing microorganisms are washed out of the system. This is achieved by setting the external conditions such as retention time, hydrogen partial pressure, temperature and pH value so that these organisms have a generation time which is longer than their hydraulic retention time in the reactor. In addition, it is possible to add inhibitors which selectively hinder the growth of the 1,3-propanediol decomposing microorganisms. To inhibit sulphate-reducing microorganisms it is possible to add for example 1,8-dihydroxyanthraquinone (EP0525073) or molybdate.

Figure 6:
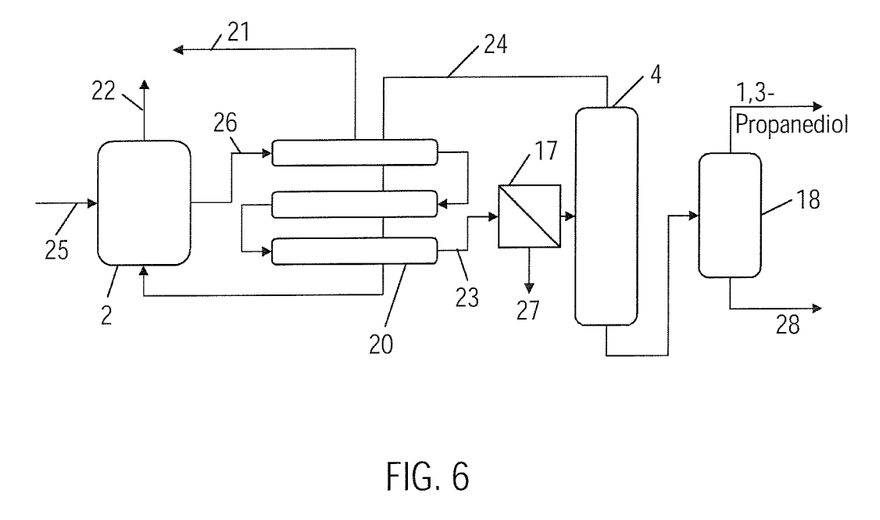
FIG. 6: a circuit diagram for the purification of 1,3-propanediol.

FIG. 6 shows a preferred embodiment for purification of 1,3-propanediol without separation of glycerol and 1,3-propanediol. This purification may be used for processes in which 1,3-propanediol and methane are produced in the same bioreactor, and also for two-stage processes such as for example embodiment 2 in which the methane production takes place in a second bioreactor. The plant comprises a bioreactor 2 in which glycerol is fed in via feed line 25 and converted into 1,3-propanediol. In a single-stage process, the methane formed is withdrawn from the bioreactor 2 via gas outlet line 22. From the bioreactor 2 the fermentation broth together with the surplus glycerol and the not yet recycled inhibiting metabolites are fed via outflow line 26 into the downstream reactor 20. The downstream reactor 20 is comprised of three flow pipes linked to form a cascade. The methane formed from the remaining metabolites is drawn off from the downstream reactor 20 via a degassing line 21. As described above, the downstream reactor 20 is so controlled that the 1,3-propanediol from the bioreactor 2 is not decomposed. The fermentation surplus of the downstream reactor 20 remaining after conversion of the surplus glycerol is led away for protein removal via line 23 through filter 17, which may be in the form of an ultrafiltration unit. The proteins from the fermentation broth may precipitate in the distillation column and should therefore be separated off beforehand via outlet line 27. The filtrate from the filter 17 is fed into a vacuum distillation column 4, in order to separate water and highly volatile metabolites from 1,3-propanediol and the salts. In the single-stage process described here, the condensate of water and highly volatile metabolites drawn off from the head of the vacuum distillation column is fed back into the bioreactor 2 via the return line 24. In the case of a two-stage process as in the second embodiment, the water and the highly volatile metabolites are transferred to a second bioreactor for methane fermentation. The residue collected in the bottom of the distillation column 4 is finally fed into an evaporator 18, in order to separate the 1,3-propanediol from the salts. The salts remaining in the evaporator 18 are removed through the outlet 28.

Moreover the manner in which the products may be purified and/or separated is not limited to the specific embodiments described above. Here in principle all the separation processes and apparatus for separation known to the person skilled in the art may be used. In particular it is possible to use more separation agents than indicated in the above embodiments.

5. MASS BALANCE IN THE PRODUCTION OF 1,3-PROPANEDIOL

Shown in FIG. 5 are two mathematical balance models for the mass balance of liquids (upper equation system in FIG. 5) and of gaseous substances (lower equation system in FIG. 5).

Figure 4:
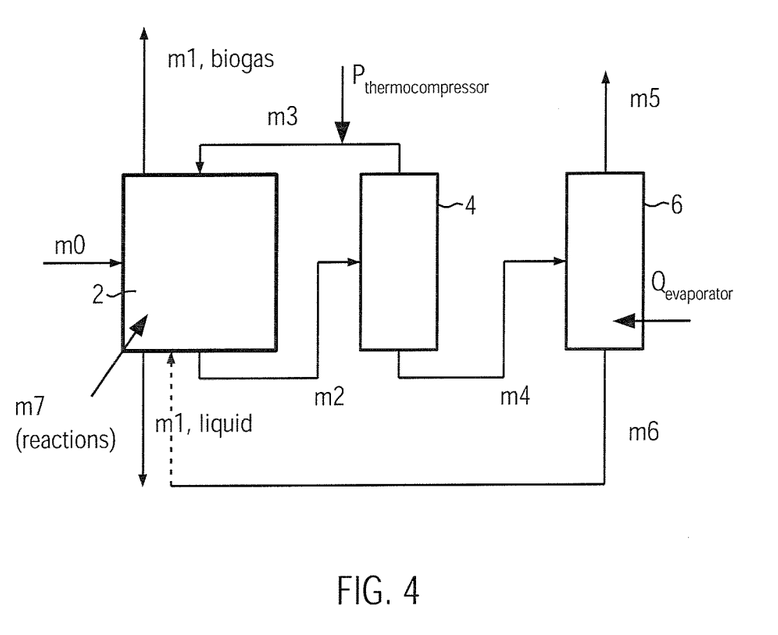
FIG. 4: a block diagram with mass flows.

FIG. 4 shows in a block diagram the mass flows with the aid of the first embodiment.

To determine the amounts of energy, a mass balance of the 1,3-propanediol production is made. The balance covers the following components: water, glycerol, 1,3-propanediol (PDO), biogas (BG), free metabolites. Aqueous glycerol solution is fed into the reactor (m0). The discharge and biogas flow is taken as one flow (m1). A circulatory flow is branched off from the reactor and fed to the evaporator. At the head of the evaporator is a thermocompressor which creates a vacuum. The vapour condensate (m3) is returned to the reactor to dilute the glycerol. In the evaporator there is a bottom flow (m4) which passes into the second separation stage, which draws off a mixture of propanediol and free metabolites through the head (m5) and an aqueous glycerol, propanediol, salt solution through the bottom (m6). This material may be pumped back into the bioreactor, but this leads to a very high product and substrate concentration in the reactor. The conversion of the products within the bioreactor 2 is simulated by feeding a reaction mass flow (m7) into the reactor, which feeds in the products and carries away the educts.

The individual equations (1) of the balance model for liquids is explained below:

$$m_0 - m_1 - m_2 + m_3 + m_7 = 0 \tag{I}$$

Equation (I) describes the balance of the substances flowing into and out of the reactor. Aqueous glycerol solution m0 is fed into the reactor. The discharge flow m1 which is not to be recycled is removed from the reactor. The circulatory flow m2 is carried away from the reactor. The vapour condensate m3 from the first column is fed into the reactor. The total of the substance flows m0, m3, m7 fed into the reactor is equal to the total of the substance flows m1, m2 removed from the reactor.

$$m_2 - m_3 - m_4 = 0 \tag{II}$$

The second equation (II) describes the balance of the liquid substances in the first column. The circulatory flow m2 to be evaporated is fed into the first column. The vapour condensate m3 resulting from evaporation is removed from the column. The concentrated bottom flow m4 is carried away from the column. The substance flow m2 in the first column is equal to the sum of the substance flows m3 and m4 taken away from the first column.

$$m_4 - m_5 - m_6 = 0 \tag{III}$$

Equation (III) describes the balance of the liquid substances fed into and removed from the second column. The concentrated bottom flow m4 is fed to the second column. The propanediol-water-metabolite mixture m5 is removed via the head of the second column. The aqueous glycerol-propanediol-salt solution m6 is carried away from the second column and may also be fed back again into the reactor. However, this is not provided for in this balance model. The substance flow m4 fed in corresponds to the total of the two substance flows m5, m6 removed.

$$m_0 = m_{input} \tag{IV}$$

Equation (IV) describes the fact that the aqueous glycerol solution m0 is the sole externally supplied educt $m_{input}$.

$$-K_1 m_2 + m_3 = 0 \tag{V}$$

Equation (V) describes the proportion of the circulatory flow m2 fed into the first column which is fed back into the reactor as recirculated water m3.

$$-K_2 m_4 + m_5 = 0 \qquad \text{(VI)}$$

Equation (VI) describes how much propanediol-water-metabolite mixture m5 is obtained from the infed bottom flow m4.

$$m_7 = m_{Reaktion} \qquad \text{(VII)}$$

Equation (VII) represents the conversion of the educts into products in the bioreactor 2.

$$m_1 - K_{purge} m_2 = 0 \qquad \text{(VIII)}$$

Equation (VIII) describes the proportion of liquid waste substances m1 which occur relative to the circulatory flow m2.

In equation 2 of FIG. 5, the balance model of the gaseous substances corresponds to the balance model of the liquids. It differs only in equation (VIII), which reads as follows:

$$m_1 = -m_{Reaktion} \qquad \text{(VIII)}$$

Equation (VIII) indicates that the methane carried away represents the reaction product.

$$P_{Thermokompressor} = m_{Wasser,3} \cdot 20 \frac{kWh}{t} \qquad \text{(equation 3)}$$

The power or the heat which is fed to and used by the compressor of the first column is calculated by equation 3. Approx. 20 kWh are needed to evaporate one tonne of water using the thermocompressor.

$$Q_{Sumpfverdampfer} = r_{0,Wasser} \cdot (m_{Wasser,5} + m_{VFA,5}) + r_{0,PDO} \cdot (m_{PDO,5} + m_{Glycerin,5}) \qquad \text{(equation 4)}$$

The electrical energy required for the evaporator of the second column is shown in equation 4. It is calculated from the evaporation heat of the individual components of the discharged aqueous substance flows m6, m5. For the metabolites and water, the mass-based evaporation enthalpy of water $r_{water}$ is used. For glycerol and propanediol the evaporation enthalpy of propanediol $r_{PDO}$ is used.

The condensation of the product flow at the head of the column, the partial recirculation and the heat requirement due to temperature difference and thermal capacity are ignored in this simplified process model.

$$Y = \frac{m_{PDO,5}}{m_{Glycerin,1}} \qquad \text{equation 5}$$

The efficiency of the plant and of the propanediol yield m5 relative to the infed glycerol solution is described in equation 5.

$$\eta_{PDO} = \frac{\Delta h^0_{c,PDO} \cdot m_{PDO,5}}{\Delta h^0_{c,Glycerin} \cdot m_{Glycerin,0}} \qquad \text{equation 6}$$

Equation 6 describes the efficiency ratio between the energy removed in the aqueous propanediol m5 and the energy supplied in the aqueous glycerol flow m0. This shows that 27% of the energy of the glycerol m0 is converted into the propanediol m5 produced.

$$\eta_{Biogas} = \frac{\Delta h^0_{c,Biogas} \cdot m_{Biogas,1}}{\Delta h^0_{c,Glycerin} \cdot m_{Glycerin,0}} \qquad \text{equation 7}$$

Equation 7 describes the efficiency ratio between the energy removed in the biogas m1 and the energy supplied in the aqueous glycerol flow m0. This shows that 65% of the energy of the glycerol m0, based on the calorific value, is converted into biogas m1.

$$\eta_{Rest} = 1 \eta_{PDO} - \eta_{Biogas} \qquad \text{equation 8}$$

Equation 8 gives the energy losses in the plant. If one adds up the energy used and deducts this figure from the energy applied, the result is the energy potential contained in the by-products. The unused energy in the glycerol-propanediol-salt solution m6 amounts to 8% of the applied initial energy of the glycerol m0.

With the aid of the equations just described, the simplified mass balance of the propanediol production may be obtained.

To obtain this balance the assumption is made that the glycerol solution fed into the reactor contains 40% glycerol and 60% water. The glycerol solution comes for example from the waste flow of a biodiesel plant.

In the first separation stage 4 approx. 80% of the water of the infed circulatory flow m2 is evaporated. Also evaporated is 99% of the biogas contained in the infed circulatory flow and 80% of the metabolites. These substances are fed back into the reactor as vapour condensate m3.

In the second column approx. 92% of the remaining water, 1% of the glycerol, 99% of the remaining biogases and 92% of the remaining metabolites are carried away in partial flow m6. 90% of the propanediol is taken away through partial flow m5 as a propanediol-water-metabolite mixture.

In the overall reaction, 90% of the infed glycerol is converted.

Approx. 1% of the total mass is removed from the reactor as waste (m1, liquid), to avoid excessive impurities.

For the parameters K, the following assumptions are made: $K_{water,1}=80\%$, $K_{glycerol,1}=0\%$, $K_{PDO,1}=0\%$, $K_{BG,1}=99\%$, $K_{VFA,1}=80\%$.
$K_{water,2}=92\%$, $K_{glycerol,2}=1\%$, $K_{PDO,2}=90\%$, $K_{BG,2}=99\%$, $K_{VFA,2}=92\%$ In the combined heat and power unit, an electrical efficiency of 40% and a thermal efficiency of 45% have been assumed.

With the assumed values and the above equations, the mass balance shown in Table 1 below is obtained:

| Mass balance: | | | | | | | |
| --- | --- | --- | --- | --- | --- | --- | --- |
| [t/h] | water | glycerin | PDO | BG | VFA | total | TS |
| $m_0$ (feed) | 6.00 | 4.00 | 0.00 | 0.00 | 0.00 | 10.00 | 40% |
| $m_1$ | 0.29 | 0.00 | 0.02 | 1.44 | 0.00 | 1.75 | 1% |
| $m_2$ | 28.57 | 0.40 | 2.14 | 0.00 | 0.02 | 31.12 | 8% |
| $m_3$ | 22.86 | 0.00 | 0.00 | 0.00 | 0.01 | 22.87 | 0% |
| $m_4$ | 5.71 | 0.40 | 2.14 | 0.00 | 0.00 | 8.25 | 31% |
| $m_5$ (product) | 5.26 | 0.00 | 1.92 | 0.00 | 0.00 | 7.19 | 27% |
| $m_6$ | 0.45 | 0.39 | 0.21 | 0.00 | 0.00 | 1.06 | 57% |
| $m_7$ | 0 | −3.6 | +2.16 | +1.4364 | +0.0036 | 0.00 | |

From a glycerol solution containing 6 t water and 4 t glycerol, approx. 1.92 t PDO-water-VFA-mixture per hour may be produced. According to equation 5, this gives a yield of 48%.

In the present example, the thermo-evaporator requires an electrical output of 0.46 MW. This corresponds to around 23% of the electricity generated from methane in the combined heat and power unit. From this it follows that 1.67 MW of electrical power may be fed into the mains network.

The bottom evaporator requires a temperature of roughly 100° C. to 200° C. The temperature of the waste gas of the combined heat and power unit is approximately 300° C. to 400° C. and the cooling of the motor of the combined heat and power unit gives out gas with a temperature of around 90° C., which may be used for heating the second column. The bottom evaporator requires heat amounting to 3.74 MW. This corresponds to around 156% of the heat available. This means that additional heat amounting to 1.61 MW must be fed into the plant. Alternatively, some of the surplus electricity is used to operate a heat pump which, starting from the temperature level of the motor cooling water, provides high temperature heat for the bottom evaporator. The plant would then be self-sufficient in energy.

5. PROCESS FOR THE PRODUCTION OF FURTHER PRODUCTS

The process and the apparatus described above may also be used for the production of other products. At the same time, provision is always made for the conversion into methane of acidic, reaction-inhibiting by-products, with the energy obtained from and the methane being utilised directly or fed back into the process.

Another product which can be made is 2,3-butanediol, in which case the substrate used is glucose and/or cellulose and/or lignocellulose, the organisms used are bacteria of the species *Klebsellia*, especially *K. oxytoca* and/or *K. pneumoniae* and/or *Enterobacter*, especially *E. aerogenes* and/or *Citrobacter* and/or *Lactobacillus*, especially *L. buchneri* and/or *Clostridium*, especially *C. pasteurianum* and/or bacilli, especially *B. polymyxia* and/or a recombinant host strain, especially *E. Coli*, while the resultant by-product or by-products is or are acetate and/or ethanol and/or formate and/or butyrate and/or succinate and/or acetate and/or acetoin and/or $CO_2$ and/or $H_2$, which are decomposed in the production of methane.

The end product may also be succinate, in which case the substrate will be glucose and/or glycerol, and the organisms used are bacteria of the species *Fibrobacter*, especially *F. succinogenes* and/or *Clostridium*, especially *C. coccoides*, and/or *Ruminococcus*, especially *R. flavefaciens* and/or *Ruminobacter*, especially *R. amylophilus*, and/or *Succinomonas*, especially *S. amylolytica* and/or *Succinivibrio*, especially *S. dextrinosolvens* and/or a recombinant host strain, especially *E. coli*. The by-product or by-products is or are acetate and/or propionate and/or formate and/or lactate and/or 2,3-butanediol and/or $CO_2$ and/or $H_2$, which are decomposed in the production of methane.

Another possible product is xylitol, in which case hemicellulose or biomass containing hemicellulose is used as substrate, and as organisms bacteria of the species *Klebsellia* and/or *Enterobacter* and/or *Citrobacter* and/or *Lactobacilli*, and/or *Clostridia* are used, with the by-product or by-products being acetate and/or ethanol and/or formate and/or butyrate and/or succinate and/or lactate and/or 2,3-butanediol and/or propionate and/or acetoin and/or $CO_2$ and/or $H_2$, which are decomposed in the production of methane.

The product made can also be acetone and/or butanol, with glucose and/or glycerol and/or starch and/or cellulose and/or carbohydrate-containing biomass and/or fats being used as substrate, and microorganisms of the species *Klebsellia* and/or *Enterobacter* and/or *Citrobacter* and/or *Lactobacilli* especially *L. buchneri* and/or *Clostridia*, especially *C. pasteurianum* and/or *C. acetobutylicum* and/or *C. beijerinkii* and/or *C. aurantibutyricum* and/or *C. tetanomorphum* and/or a recombinant host strain, especially *P. pastoris* and/or *E. coli* being used as organisms. By-products may include acetate and/or ethanol and/or formate and/or butyrate and/or $CO_2$ and/or $H_2$, which are decomposed in the production of methane.

Another product which may be made is lactate, in which case glucose and/or glycerol and/or vinasse from the ethanol production and/or milk and/or whey is used as substrate, while lactic acid bacteria of the species *Lactobacilli*, especially *L. bifermentans* and/or *L. brevi* and/or *L. fermentum* and/or *L. delbrueckii* and/or *L. caseii* are used as organisms, with by-products which may include acetate and/or ethanol and/or $CO_2$, which are decomposed in the production of methane.

The product may also be 1,2-propanediol, with glucose and/or glycerol used as substrate, and bacteria of the species *Klebsellia* and/or *Enterobacter* and/or *Citrobacter* and/or *Lactobacilli* especially *L. buchneri* and/or *Clostridia*, especially *C. pasteurianum* and/or *Thermoanaerobacterium*, especially *T. thermosaccharolyticum* and/or a recombinant host strain, especially *E. coli* are used, while by-products may include acetate and/or ethanol and/or formate and/or propionate and/or butyrate and/or $CO_2$ and/or $H_2$, which are decomposed in the production of methane.

Where glycerol is the end product, glucose and/or carbohydrate-based biomass will be used as substrate, and as organisms microorganisms of the species *Pichia*, especially *P. farrnosa* and/or *Saccharomyces*, especially *S. rouxii* and/or a recombinant host strain, especially *E. coli* are used, with by-products including acetate and/or ethanol and/or methanol and/or formate and/or $CO_2$ and/or $H_2$, which are decomposed in the production of methane.

The invention claimed is:

1. A process for the microbial production of 1,3-propanediol and methane by a co-culture of microorganisms in a bioreactor, comprising:
   a) producing 1,3-propanediol in an anaerobic bioreactor from a substrate using a producer microorganism, wherein during the production of 1,3-propanediol at least one byproduct selected from the group consisting of alcohols, aldehydes, acids, hydrogen, carbon dioxide, and combinations thereof is also produced by the producer microorganism,
   b) producing methane using a methanogen, wherein during the production of the methane at least one byproduct from step (a) is consumed wherein said byproduct inhibits the production of 1,3-propanediol by said producer microorganism, and
   c) purifying the 1,3-propanediol.

2. The process of claim 1, wherein the producer microorganism is a species of a genus of bacteria selected from the group consisting of *Klebsiella Enterobacter, Citrobacter, Lactobacilli, Clostridia*, and combinations thereof, and wherein the byproducts produced are selected from the group consisting of acetate, ethanol, formate, butyrate, succinate, lactate, 2,3-butanediol, carbon dioxide, hydrogen, and combinations thereof.

3. The process of claim 1, wherein the methane is fed to an energy converter, which converts the methane into at least one of electrical energy and heat.

4. The process of claim 3, wherein the heat or electrical energy produced is used in the bioreactor or to purify the 1,3-propanediol.

5. The process of claim 1, wherein the purification of 1,3-propanediol produces a vapor condensate which is returned to the bioreactor.

6. The process of claim 1, further comprising transferring the contents of the bioreactor to a downstream reactor wherein remaining substrate and byproducts are used to produce 1,3-propanediol and methane.

7. The process of claim 1, wherein the co-culture further comprises an acetogenic bacterium, wherein the acetogenic bacterium converts byproducts of the 1,3-propanediol producing microorganism into substrates suitable for the methanogen.

8. The process of claim 7, wherein the acetogenic bacterium is a species of a genus selected from the group consisting of *Acetobacter, Clostridia*, and combinations thereof.

9. The process of claim 7, wherein the acetogenic bacterium is a homoacetate fermenter, and wherein the homoacetate fermenter is a hydrogen sink.

10. The process of claim 7, wherein the acetogenic bacterium converts the byproducts to acetate.

11. The process of claim 7, wherein nutrients and substrates obtained during the purification of the 1,3-propanediol, are fed back into the bioreactor.

12. The process of claim 11, wherein the substrate obtained during purification is glycerol.

* * * * *